United States Patent [19]

Davies et al.

[11] 4,279,894
[45] Jul. 21, 1981

[54] STREPTOMYCES METABOLITE

[75] Inventors: David H. Davies, Macclesfield; Geoffrey L. F. Norris, Sandbach, both of England

[73] Assignee: Imperial Chemical Industries Limited, London, England

[21] Appl. No.: 60,682

[22] Filed: Jul. 25, 1979

[30] Foreign Application Priority Data

Aug. 3, 1978 [GB] United Kingdom ............... 32172/78

[51] Int. Cl.³ .............................................. A61K 35/00
[52] U.S. Cl. .................................... 424/122; 435/169
[58] Field of Search ........................ 424/122; 435/169

Primary Examiner—Jerome D. Goldberg
Attorney, Agent, or Firm—Cushman, Darby & Cushman

[57] ABSTRACT

The invention relates to a novel metabolite, M.139603, of the empirical formula $C_{35}H_{53}O_8Na$, which is obtained from the aerobic fermentation of a novel Streptomyces species, NCIB 11426, and to the corresponding free acid form thereof, $C_{35}H_{54}O_8$. M.139,603 reduces the proportion of methane produced by the "digestion" of food in the rumen of ruminant animals and increases the proportion of propionate to acetate in the rumen contents. The compound is therefore useful for increasing the growth rate of ruminant animals, and/or for increasing their efficiency of food conversion. The compound also possesses activity against Gram positive micro-organisms, and against coccidia, for example *Eimeria tenella*.

6 Claims, 4 Drawing Figures

STREPTOMYCES METABOLITE

This invention relates to a metabolite, M.139,603, obtainable from the aerobic culture of *Streptomyces longisporoflavus* which is apparently a novel compound of the formula $C_{35}H_{53}O_8Na$. M. 139,603 is a sodium salt, and the invention also relates to the corresponding "free acid" and other alkali metal salts which can be derived therefrom. The compounds are effective in reducing the proportion of methane produced by ruminal fermentation, and increasing the proportion of propionic acid in bovine rumen fluid, and are therefore believed to possess growth promoting properties in ruminants, it being well known that other chemical compounds which increase the level of propionic acid in rumen fluid result in increased growth rates when fed to cattle or sheep. The novel compounds of the invention also possess antibacterial activity against Gram positive organisms, and anticoccidicial activity against *Eimeria tenella* in an in vitro test.

Figure 1:
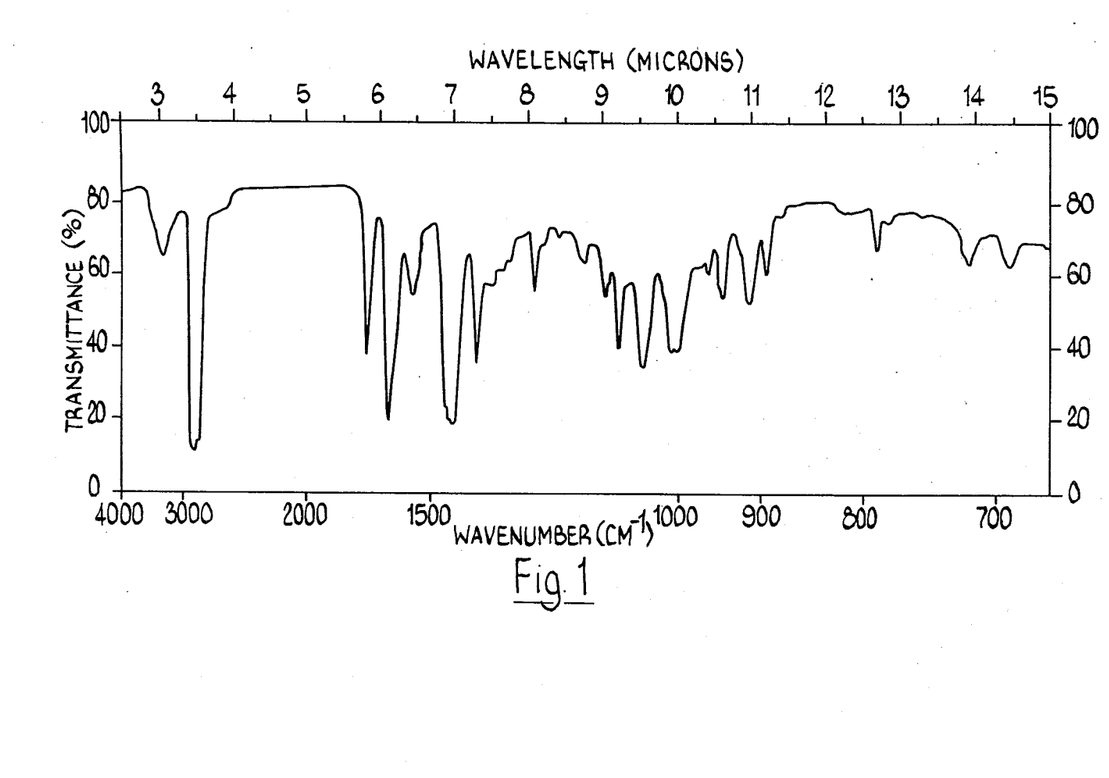
Figure 2:
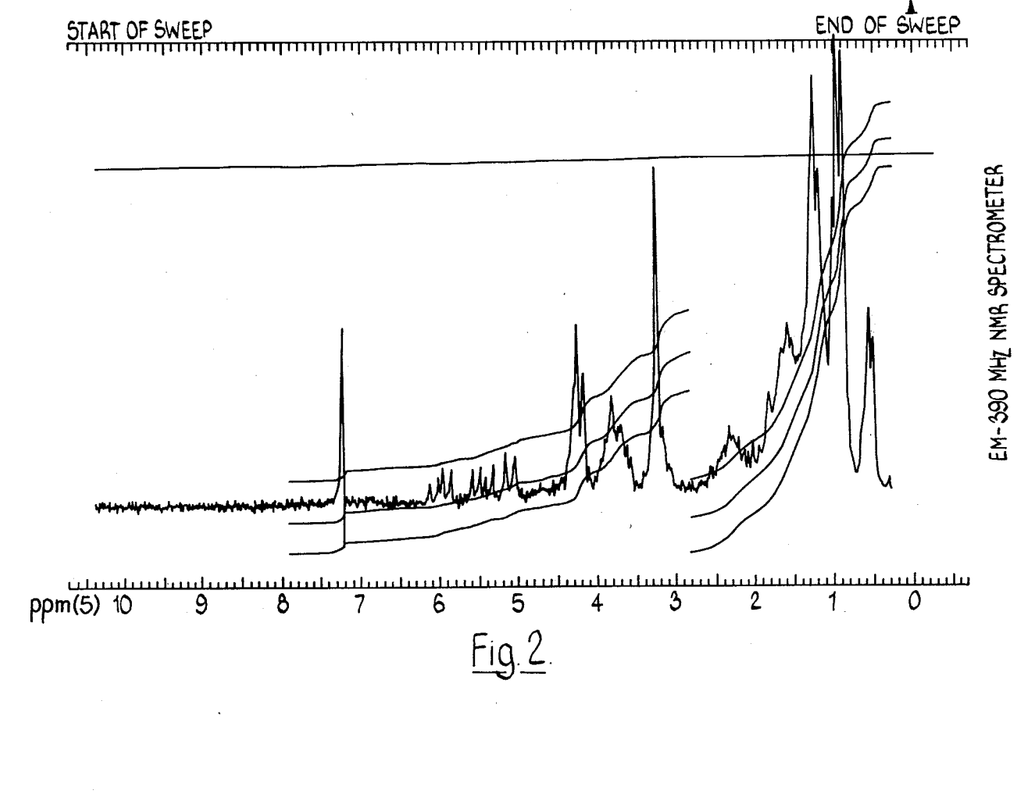

According to the invention there are provided the compound M.139,603 which has the following characteristics:

(a) molecular formula $C_{35}H_{53}O_8Na$ as indicated by mass spectrometry, which shows a molecular ion, $M^+$, of mass 624,361 (calculated for $C_{35}H_{53}O_8Na = 624.364$), and by elementary analysis: C=67.5, H=8.8%, (calculated for $C_{35}H_{53}O_8Na$-C=67.3, H=8.5%);

(b) infra-red spectrum in nujol mull, as shown in FIG. 1 containing characteristic absorptions at 3300, 1725, 1645, 1565 and 915 $cm^{-1}$;

(c) proton magnetic resonance spectrum in deuteriochloroform as shown in FIG. 2;

(d) ultra-violet spectrum in ethanol solution shows characteristic absorptions at 234 nm ($\epsilon=12900$) and 272 nm ($\epsilon=10800$);

(e) melting point 176°-8° C.;

(f) $[\alpha]_D^{23}=-82°$ (c=0.2 in methanol);

and the corresponding "free acid" form thereof of the molecular formula $C_{35}H_{54}O_8$, characterised by $R_F=0.55$ (approximately) on thin layer chromatography on silica gel (Merck's "Kieselgel 60F-254"—trade mark), 0.25 mm. thickness, developed with a mixture of diethyl ether, methanol and formic acid in the proportion 95:4:1 by volume; UV in ethanol 274 nm ($\epsilon=13900$), broad;

and other alkali metal salts which can be derived therefrom.

According to a further feature of the invention there is provided a process for the manufacture of the above compounds of the invention which comprises culturing an M139,603—producing strain of *Streptomyces longisoporoflavus*, or an M.139,603—producing variant or mutant thereof, in an aqueous nutrient medium containing a source of assimilable carbon, under shaken aerobic conditions at a temperature of between 22° and 32° C., extracting the fermentation mixture thus obtained with a water-immiscible organic solvent by conventional means, and evaporating the solvent, whereafter if desired the sodium salt, M.139,630, may be converted to the "free acid" and the "free acid" may be converted to other alkali metal salts, by conventional methods.

A suitable M.139,603—producing strain of *S. longisporiflavus* is that identified as NCIB 11426, which is available without restriction from the National Collection of Industrial Bacteria, Ministry of Agriculture, Fisheries and Food, Torry Research Station, 135 Abbey Road, Aberdeen AB9 8DG, Scotland, and which has the following description:

[The media used are made up in accordance with the recipes for the 'International Streptomyces Project' (ISP) and are as described by Shirling, E.G. & Gottlieb D (International Journal of Systematic Bacteriology, 16, (3), 313-340, 1966)]. Conditions of incubation—ca. 25° C.—daylight.

ISP1 Tryptone yeast (but with added agar).
- 5 days- Thin, slightly wet, velvety, light fawn.
  Reverse uncoloured.
- 13 days- Thin velvety - slightly granular, light fawn.
  Reverse uncoloured.

ISP2 Yeast extract/Malt extact agar.
- 5 days- Thin, velvety, light grey.
  Reverse - very pale yellow fawn.
- 13 days- Fair, raised and wrinkled, velvety, light yellow/brown/grey.
  Reverse - fawn.

ISP3 Oatmeal agar.
- 5 days- Sparse to thin, velvety, light yellow/grey
  Reverse not visible.
- 13 days- Thin, slightly raised, velvety, light grey.
  Reverse not visible.

ISP4 Inorganic salts - starch agar.
- 5 days- Thin, light fawn, slightly granular.
  Reverse uncoloured.
- 13 days- Thin, slightly wet, fawn.
  Reverse more or less uncoloured.

ISP5 Glycerol - asparagine agar.
- 5 days- Thin, slightly granular, light fawn.
  Reverse - uncoloured.
- 13 days- Thin, velvety, light grey.
  Reverse - uncoloured.

ISP7 Tyrosin agar.
- 5 days- Sparse to thin, slightly granular, velvety, light fawn/grey.
  Reverse uncoloured.
- 13 days- Thin, velvety, slightly raised, fawn.
  Reverse - fawn/grey.

ISP9 - Carbon utilisation agar.

| | | | Score |
|---|---|---|---|
| 15 days | No carbon | Very sparse, submerged | − |
| | Glucose | Thin/Fair, velvety, fawn | + |
| | Arbinose | Sparse | ± |
| | Fructose | Thin, velvety, fawn | + |
| | Inositol | Very sparse | − |
| | Mannitol | Thin, velvety | + |
| | Raffinose | Very sparse | − |
| | Rhamnose | Sparse | ± |
| | Xylose | Sparse | ± |

On ISP7, in age, the culture generally becomes more pinkish fawn, but shows some areas of darker colouring, associated with heavier sporulation.

General

No Melanins are produced.
No reverse pigments are produced.
No soluble pigments are produced.
Spores are borne in open and tight spirals, often separated from the main axis by a straighter supporting 'hypa' or perhaps chain of spores. The spores themselves are difficult to see by normal microscopy being very closely joined together. The spore walls (E.M. on 4% uranyl acetate preparation) are smooth.

This strain of *S. longisporoflavus* is also available without restriction from the Centraalbureau voor Schimmelcultures, PO Box 273, Oosterstraat 1, 3740 AG Baarn, Netherlands, under reference CBS 312.79.

According to a further feature of the invention there is provided *Streptomyces longisporoflavus* NCIB 11426, and M.139,603—producing variants and mutants thereof.

According to a further feature of the invention there is provided the fermentation mixture which is obtained by culturing an M.139,603—producing strain of *Streptomyces longisporoflavus* NCIB 11426, or an M.139,603—producing variant or mutant thereof.

According to a further feature of the invention there is provided an extract which is obtained by culturing an M.139,603—producing strain of *Streptomyces longisporoflavus* NCIB11426, or an M.139,603—producing variant or mutant thereof, as described above, and extracting the fermentation mixture with water-immiscible organic solvent, for example ethyl acetate.

According to a further feature of the invention there is provided the compound M.139,603, whenever manufactured by the culture of *Streptomyces longisporoflavus* NCIB 11426, or a variant or mutant thereof, as described above, or by an obvious equivalent thereof.

The "free acid" corresponding to the sodium salt, M.139,603, may be obtained by acidifying a solution of M.139,603 and extracting the acidic solution with a water-immiscible organic solvent; and other alkali metal salts may be obtained by treating a solution of the "free acid" with an appropriate alkali metal hydroxide, for example lithium hydroxide, potassium hydroxide, caesium hydroxide or rubidium hydroxide. If sodium hydroxide is used, M.139,603 is regenerated thus demonstrating that no structural change is involved in these reactions.

As stated above, the compounds have the effect of increasing the proportion of propionic acid in rumen fluid, and in particular increase the proportion of propionic acid at the expense of methane and/or acetic acid. This is known to be a desirable effect in ruminant nutrition, because propionic acid is a much more efficient precursor of glucose, from which the animal derives its energy and growth, than is acetic acid; while that part of the animals' food intake which is converted to methane is simply lost to the animal, the methane being excreted by eructation. Thus, the modification of rumen metabolism achieved by the compounds of the invention is a most useful effect, and is believed to increase the rate of growth and the food conversion efficiency of ruminant animals.

Thus, according to a further feature of the invention there is provided a method for use in the husbandry of domestic ruminant animals, for increasing their rate of growth and/or increasing the efficiency of their food conversion, which comprises orally administering to the animals a compound, fermentation product or extract of the invention as described above.

In the method of the invention, the compounds of the invention are preferably orally administered to the animals as a supplement to their normal diet, that is to say, in admixture with an ordinary solid foodstuff, in feedblocks or salt-licks, dissolved in the drinking water or, for young animals such as lambs or calves, dissolved in whole milk or skim milk. The compounds of the invention are incorporated into food, feedblocks, salt-licks, drinking water, whole milk or skim-milk to such an extent that each treated animal will ingest from 0.01 mg/kg. body weight to 30 mg./kg. body weight per day, preferably from 0.01 mg./kg. to 10 mg./kg. per day, of a compound of the invention.

The compounds of the invention may alternatively be orally administered to animals in the form of a slow-release, intra-ruminal pellet or bolus, such that the animal will absorb a similar quantity per day of the compounds of the invention.

The animals may receive the compounds of the invention for substantially the whole of their growing period, or for only a part of their growing period, for example the early part and/or the period leading up to slaughter. The increase in growth rate achieved by practising the method of the invention enables animals reared for meat to be brought to market weight or slaughter weight in a shorter growing period than normal or it enables heavier animals to be produced at the end of the normal growing period. The improved efficiency of food conversion achieved by practising the method of the invention enables treated animals to reach any desired weight while consuming less food than untreated animals grown to the same weight. At optimum growth promoting inclusion levels, no indication of any toxic effect due to the compounds of the invention is observed.

According to a further feature of the invention, there is provided a composition which comprises a compound, fermentation product or extract of the invention, together with a solid or liquid, edible non-toxic diluent or carrier.

A suitable liquid diluent or carrier is, for example, drinking water, whole milk or skim milk.

A suitable solid, edible, non-toxic diluent or carrier may be, for example, a conventional nutritionally balanced ruminant feedstuff, for example a typical cattle or sheep diet consisting of cereal products, such as barley meal, maize meal or wheat feed, nut and seed products, such as decorticated ground nut cake or cotton seed cake, or extracted cotton seed cake, together with minor amounts of, for example feather meal, seaweed meal, bone meal, bone flour, chalk, salt, molasses, urea, vitamines and trace minerals; or it may be an inert solid diluent or carrier of no energy value, for example kaolin, talc, calcium carbonate, fuller's earth, attapulgus clay, ground oyster shells or ground limestone; or it may be starch or lactose.

The composition of the invention may take the form of a supplemented feedstuff for direct feeding to animals, in which case it will contain from 5 ppm to 3000 ppm of the compound of the invention in admixture with a conventional ruminant feedstuff; or it may take the form of a concentrated premix for dilution with a conventional ruminant feedstuff to produce a supplemented feedstuff suitable for direct feeding, and such a premix will contain from 0.3% w/w to 50% w/w of the compound of the invention in admixture with either a conventional, nutritionally balanced ruminant feedstuff, an inert solid diluent of no energy value, for example ground limestone, or starch or lactose.

In all the compositions of the invention described above, the compound of the invention may, of course, be replaced by the fermentation mixture of the invention, or an extract of the invention, containing an equivalent quantity of M.139,603.

According to a further feature of the invention there is provided a process for the manufacture of a solid composition of the invention which comprises uniformly mixing a compound, fermentation mixture or extract of the invention with a solid, edible, non-toxic diluent or carrier.

The compound of the formula I is preferably serially diluted with the diluent or carrier in two or more successive stages, to ensure even mixing.

Also as stated above, the compounds of the invention possesses anticoccidial activity. This is demonstrated by a tissue culture test in chick kidney cells, inoculated with sporozoites of *Eimeria tenella*, in accordance with the standard test procedure described in Journal of Parasitology, volume 58, pages 664–668 (1972). In this test, M.139,603 prevents growth of the sporozoites at a concentration of $\leq 0.001$ parts per million, and shows toxic effects on the host cells only at a concentration of $\geq 0.33$ parts per million.

The compound M.139,603 also possesses Gram positive antibacterial properties, and, by way of example only, has been shown to prevent the growth of *Staphylococcus aureus, Streptococcus faecalis, Clostridium welchii* and *Corynebacterium acne* at a concentration of $\leq 10$ µg. per ml., and may therefore be used as a growth promoter in non-ruminant animals, for example poultry and pigs.

The invention is illustrated but not limited by the following Examples:

EXAMPLE 1

Streptomyces species NCIB 11426 was grown in a 500 ml. Erlenmayer flask tryptone-yeast agar, containing:

Tryptone—"Oxoid" L42 (trade mark), 0.5% w/v
yeast extract—"Oxoid" L21 (trade mark), 0.3% w/v which had been presterilised by autoclaving for 20 minutes at 120° C. The pH of the medium was approximately 7.0. The flask was shaken at 25° C. for 120 hours on a rotary shaker.

The contents of the flask were then used to inoculate a further 10 similar flasks, each containing 200 ml. of the following medium:

| | |
|---|---|
| glucose syrup | 3.0% w/v |
| calcium carbonate | 0.25% w/v |
| sodium chloride | 0.5% w/v |
| magnesium sulphate heptahydrate | 0.05% w/v |
| minor elements concentrate | 0.1% v/v |
| bacteriological peptone ("Oxoid" L37 - trade mark) | 0.1% w/v |
| beef extract powder ("Oxoid" L29, "Lab Lemco" - trade mark) | 0.5% w/v |
| de-ionised water | to 100 |

The pH was adjusted to 7.2, and the medium was presterilised by autoclaving at 120° C. for 20 minutes. The inoculated flasks were shaken at 25° C. for 120 hours on a rotary shaker, and the contents of the flasks were then pooled and adjusted to pH 3 by the careful addition of 0.1 N hydrochloric acid. The medium was extracted with ethyl acetate (2×600 ml.), the extracts were combined and dried over sodium sulphate, and the solvent was evaporated to give an oily residue (290 mg).

The ethyl acetate extract was purified by preparative layer chromatography on two silica plates (Merck's "Kieselgel" 60F-254—trade mark, 20×20 cm., 2 mm. thick) using ethyl acetate as the eluent. The band at $R_F=0.39$ (approximately) was scraped from the plates and extracted with ethyl acetate and the solvent was evaporated to give a viscous gum (21 mg.), which demonstrated in vitro antibacterial activity versus *S. aureus*.

This active fraction was further purified by preparative layer chromatography on one silica gel plate (Merck's "Kieselgel" 60F-254 20×20 cm., 0.25 mm. thick) using a mixture of diethyl ether, methanol and formic acid in the ratio 95:4:1 (by volume) respectively. The band at $R_F=0.55$ (approximately) was scraped from the plate and extracted with ethyl acetate to give, after evaporation of the solvent, a viscous gum (9 mg.). The gum was converted to a sodium salt, M.139,603, by shaking a chloroform solution with a solution of sodium hydroxide (0.1 M). The chloroform layer was separated and dried over sodium sulphate, and the solvent was evaporated to give M.139,603 as a white solid (8 mg.), m.p. 129°–132° C., the infra-red spectrum (FIG. 1) demonstrated the following maxima: 3300, 1725, 1645, 1565 and 915 cm.$^{-1}$; Elemental analysis: Found, C=67.5, H=8.8%; calculated for $C_{35}H_{53}O_8Na$, C=67.3, H=8.5. Mass spectrum: $M^{\pm}=624.361$, calculated for $C_{35}H_{53}O_8.Na=624.364$. $R_F=0.39$ (thin layer chromatography on Merck's 60F-254, 0.25 mm. plates developed with ethyl acetate, visualised as a brown spot after spraying with 3 N sulphuric acid and heating at 100° C. The proton magnetic resonance spectrum in deuteriochloroform is reproduced as FIG. 2.

EXAMPLE 2

The ability of M.139,603 to inhibit the production of methane in the rumen of ruminant animals, and to increase the proportion of propionate at the expense of acetate (Ac/Pr) in the volatile fatty acids (VFA) produced, is demonstrated as follows:

Rumen fluid is collected on a regular routine basis from two steers, which are fed on the same hay-plus-concentrate diet. Sampling time is standarised as far as possible, and the fluid from the two animals is pooled on a 50/50 basis. Large particulate matter is removed by filtering the pooled fluid through four layers of muslin cloth. The filtrate is then diluted in the ratio of one volume of filtrate to three volumes of an artificial rumen fluid (prepared as described by G. L. Bales et al., Journal of Diary Science, 1976, volume 59, page 1850, but omitting acetic acid), and the pH of the mixture is adjusted to 6.9–7.0 with saturated aqueous sodium carbonate solution. Aliquots (50 ml.) of this mixture are dispensed into 100 ml. conical flasks containing dried ground hay (0.5 g.), and each flask is used to test a test compound at a particular concentration.

The test compound is added to the conical flask as a solution in ethanol, the flask is flushed with carbon dioxide gas, stoppered with a suba-seal, and incubated at 39° C. for 15–16 hours. After one hour, a narrow bore needle is inserted through the suba-seal to relieve the gas pressure, and the needle is withdrawn 30 minutes before the incubation is ended. Fermentation is then stopped by placing the flask in ice, and after 15 minutes cooling, the gas over the liquid is analysed for methane by gas chromatography. The flask contents are then filtered through a previously dried sintered glass funnel. Three samples of the filtrate are analysed by gas chromatography for VFAs, and by comparison with the previously determined, pre-incubation level of VFAs, the net VFAs (acetate and propionate) produced during the incubation is determined.

The following results were obtained, expressed as % if control values obtained when no test compound was employed. Monensin, a known growth promoter acting by an effect on the rumen, is included as a positive control.

| Compound | Concentration μg. per ml. | Methane - % relative to control | Acetate/ propionate ratio -% relative to control |
|---|---|---|---|
| M.139,603 | 1.0 | 58 | 62 |
|  | 0.3 | 72 | 64 |
|  | 0.1 | 87 | 70 |
| Monensin | 1.0 | 67 | 79 |
|  | 0.3 | 90 | 87 |
|  | 0.1 | 100 | 95 |

EXAMPLE 3

*Streptomyces longisporoflavus* NCIB 11426 was grown as slope cultures on ISP-7 agar (45 ml.) for 7 days at 30° C. Three such slopes were individually scraped into three flasks with 100 ml. of sterile water, and the suspensions so obtained were used to inoculate three 2 liter flasks, each containing 1 liter of the following medium:

| glycerol | 3.0% | w/v |
|---|---|---|
| bacteriological peptone ("Oxoid" L-37-trademark) | 2.0% | w/v |
| $KH_2PO_4$ | 0.024% | w/v |
| $MgSO_4 . 7H_2O$ | 0.02% | w/v |
| minor element concentrate | 0.1% | v/v |
| chalk | 0.1% | w/v |
| deionised water | to 1 liter | | which had been pre-sterilised by autoclaving at 120° C. for ½ hour, the pH being approximately 6.7.

The three two liter flasks thus prepared were shaken at 30° C. for 3 days on a rotary shaker. The contents of the three flasks were then combined, and used to inoculate a stainless steel fermenter containing 30 l. of sterilised medium made up of the following:

| glycerol | 3.0% | w/v |
|---|---|---|
| soya flour BSP 70 | 1.0% | w/v |
| chalk | 0.25% | w/v |
| cerelose | 3.0% | w/v |
| NaCl | 0.5% | w/v |
| $MgSO_4 . 7H_2O$ | 0.05% | v/v |
| minor element concentrate | 0.1% | w/v |
| distilled water | to 30 liter | |

The fermenter contents were stirred at 30° C. for 70 hours, using a turbine with 4 flat blades rotating at 350 r.p.m., and aerated at a rate of 15 l. per minute. 30 Mls. of "Silcolapse" (trademark) a silicone antifoam, had been added to the mixture before autoclaving. The pH at harvest was 7.9 and the resulting fermentation mixture (22 liters) was mixed and agitated with an equal volume of ethyl acetate. After 30 minutes, the mixture was separated in a centrifugal separator, and the ethyl acetate extract (approximately 18 l.) was dried over anhydrous sodium sulphate and filtered. The filtrate was concentrated under reduced pressure to yield an oily residue (10.7 g.).

M.139603 was obtained from the above concentrate by the following procedure:

The oily residue (10.7 g.) was dissolved in the minimum volume of ethyl acetate, and the resulting solution was applied to the top of a column of neutral alumina (Woelm N, 200 g. 18 cm x 4 cm.) made up as a slurry with ethyl acetate. The column was first eluted with ethyl acetate, followed by 50% v/v mixture of ethyl acetate and methanol, and finally with methanol. The following fractions were collected after the solvent front had emerged from the column:

| Fraction No. | Volume | Eluent |
|---|---|---|
| 1 | 150ml. | ethyl acetate |
| 2 | 150ml. | " |
| 3 | 150ml. | " |
| 4 | 150ml. | " |
| 5 | 150ml. | ethyl acetate- methanol 50% v/v |
| 6 | 150ml. | " |
| 7 | 150ml. | " |
| 8 | 150ml. | " |
| 9 | 200ml. | methanol |
| 10 | 200ml. | " |
| 11 | 200ml. | " |

Fractions 7-11 inclusive were shown, by thin-layer chromatography on silica gel, developed with 20% v/v acetone in petroleum ether (b.p. 60°-80° C.), to contain M.139603 ($R_F \sim 0.22$) and they were thus combined and evaporated to give a viscous gum (840 mg.) which was further purified by preparative layer chromatography on silica (Merck's "Kieselgel 60F250"—trade mark, 40 cm. ×20 cm. 2 mm thick) using as eluent a mixture of 20% v/v acetone in petroleum ether (b.p. 60°-80° C.). The u.v. visible band at $R_F \sim 0.22$ (approximately) was scraped from the two plates and extracted with ethyl acetate, and the extract was evaporated to dryness to give a viscous gum (240 mg), which crystallised on addition of petroleum ether (b.p. 60°-80° C.). This material was recrystallised from petroleum ether (b.p. 60°-80° C.) to give M.139603 as colourless crystals which were flitered off and dried (210 mg.), m.p. 176°-178° C. The ultra violet spectrum in ethanol showed absorptions at 243 nm ($\epsilon = 12900$) and 272 nm ($\epsilon = 10800$). The infra-red and nuclear magnetic resonance spectra were identical with those obtained from the product of Example 1.

EXAMPLE 4

Figure 3:
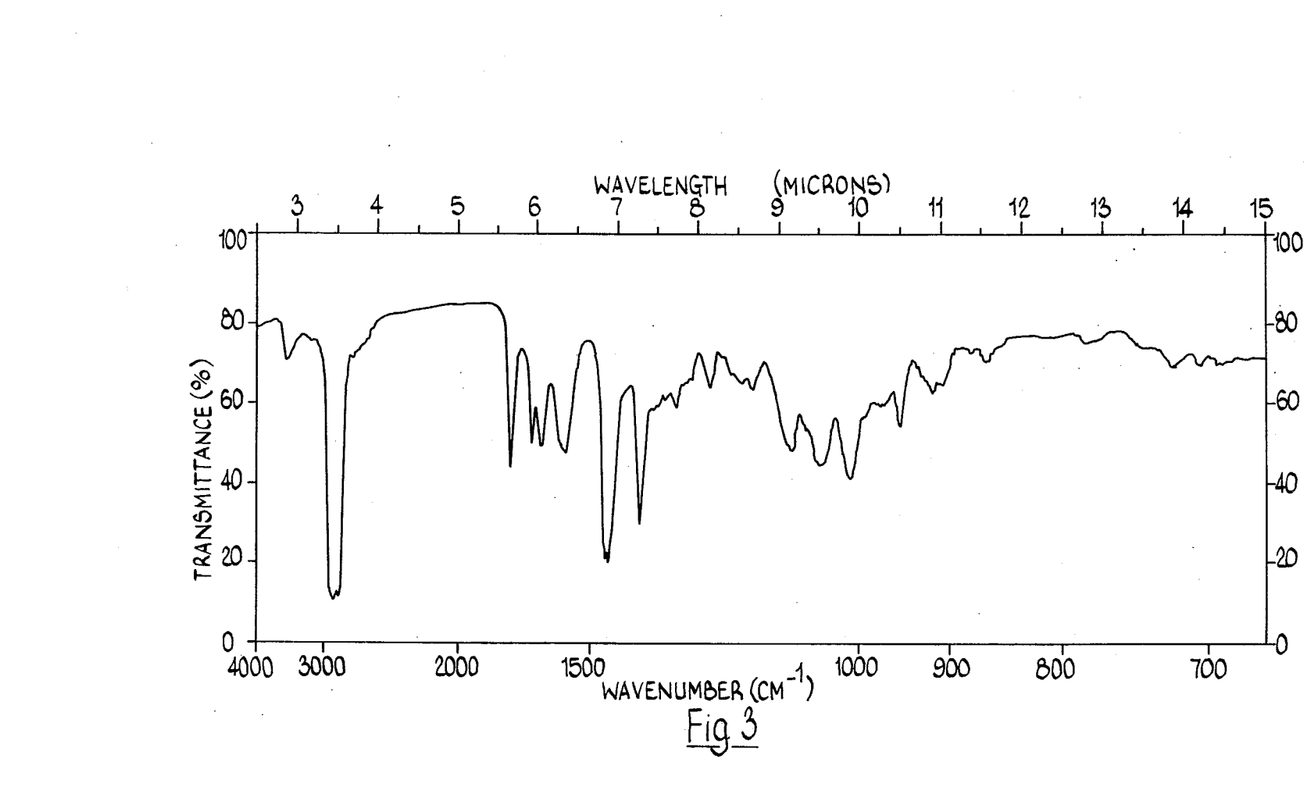
Figure 4:
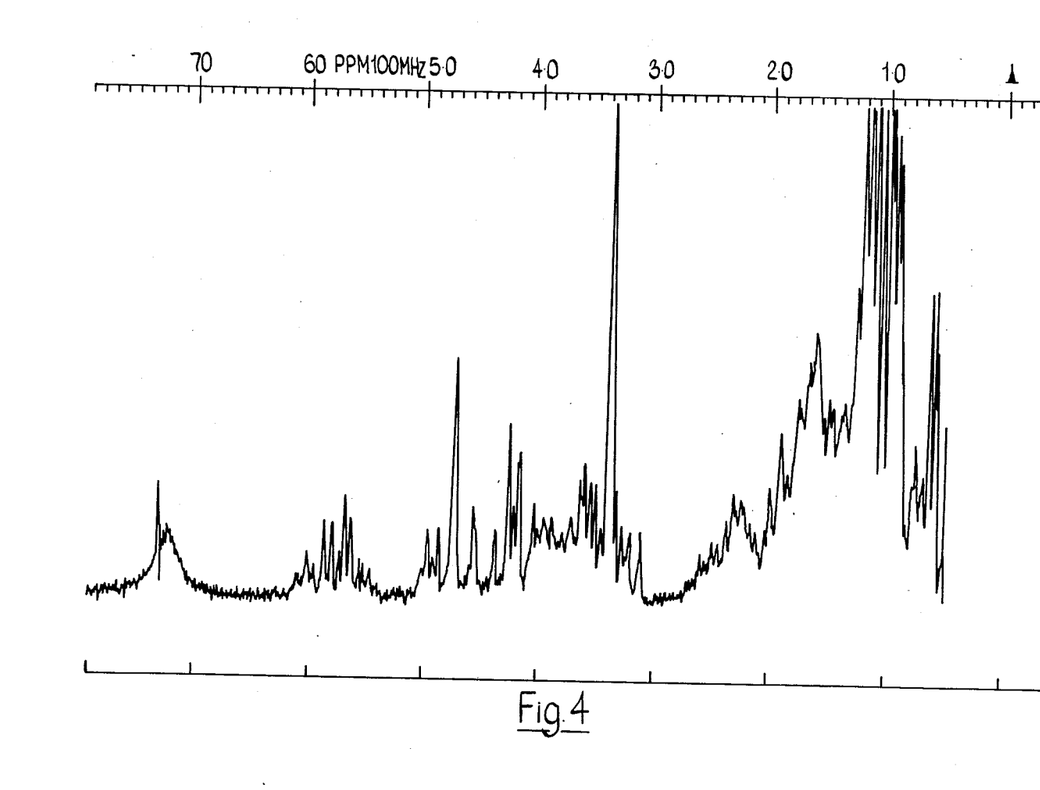

M.139603 (40 mg.) was dissolved in a mixture of acetone (10 ml.) and water (2 ml.), 1 ml. of 2 N. hydrochloric acid was added, and the mixture was stirred vigorously for 5 minutes. Distilled water (20 ml.) was added, and the mixture was extracted into dichloromethane ($2 \times 10$ ml.). The organic layer was separated and washed with 2 N hydrochloric acid followed by distilled water. The dichloromethane layer was then concentrated to give a viscous gum (33 mg.), of the "free acid" equivalent to M.139603. Elemental analysis Found: C=69.5, H=9.1. Calculated for $C_{35}H_{54}O_8$: C=69.8, H=9.0; I.R. spectrum in nujol mull, as shown in FIG. 3, containing characteristic absorptions at 3500, 1765, 1685, 1650, 1575 cm$^{-1}$; the proton magnetic resonance spectrum in deuteriochloroform is shown in FIG. 4.

EXAMPLE 5

The "free acid", equivalent to M.139603 (30 mg.) was dissolved in a mixture of tetrahydrofuran (7 ml.) and water (1 ml.). An alkali metal hydroxide, XOH (2 N, 2 ml.) was added to the aqueous tetrahydrofuran mixture which was then stirred vigorously for 10 minutes. Water (10 ml.) was added, and the solution was extracted into ether ($2 \times 15$ ml.). The ether extracts are combined and evaporated to give the akali metal salts corresponding to the sodium salt, M.139603.

When X=potassium, the potassium salt is generated, m.p. 146°–150° C., molecular formula $C_{35}H_{53}O_8.K$ as indicated by mass spectrometry, which shows a molecular ion, $M^+$, of mass 640.335 (calculated for $C_{35}H_{53}O_8.K=640.338$ ), and by elemental analysis: Found, C=65.7%, H=8.5%, (calculated for $C_{35}H_{53}O_8.K$: C=65.6%, H=8.3%).

When X=rubidium the rubidium salt is formed, m.p. 95°–120° C., molecular formula $C_{35}H_{53}O_8.Rb$, as indicated by mass spectrometry, which shows a molecular ion, $M^+$, of mass 686.279 (calculated for $C_{35}H_{53}O_8.Rb=686.286$).

EXAMPLE 6

The ability of M.139603 to increase the proportion of propionate at the expense of acetate in the ruminal fluid of sheep was demonstrated as follows:

Twenty-three sheep were housed individually and fed the same diet of 1 kg. of dried grass cubes per animal per day, split into two feeds per day. The animals were allocated randomly to 13 as negative controls, 5 as positive controls using monensin, a known rumen manipulator, and 5 to be dosed M.139603. The treated animals were given monensin or M.139603 orally at a rate of 0.5 mg./kg. on each of four successive days, and samples of rumen fluid were collected by stomach tube 6 hours after treatment on day 4. The rumen fluid samples were then analysed for acetate and propionate as described in Example 2. The results obtained were as follows:

| Treatment groups | Molar % of total VFAs. | |
|---|---|---|
| | acetate | propionate |
| Negative control | 69.9 | 19.8 |
| Positive control - monensin 0.5mg./kg. | 57.1 | 32.3 |
| M.139603 - 0.5mg./kg. | 54.2 | 39.9 |

The acetate response for M.139603 is significant at $p<0.02$ compared with the positive control, monensin; and the propionate response for M.139603 is significant at $p<0.001$ compared with the positive control, monensin.

What we claim is:

1. The compound M.139603 which has the following characteristics:
    (a) molecular formula $C_{35}H_{53}O_8Na$ as indicated by mass spectrometry, which shows a molecular ion, $M^+$, of mass 624.361 (calculated for $C_{35}H_{53}O_8.Na=624.364$), and by elementary analysis; C=67.5, H=8.8%, (calculated for $C_{35}H_{53}O_8.Na$—C=67.3, H=8.5%);
    (b) infra-red spectrum in nujol mull, as shown in FIG. 1, containing characteristic absorptions at 3300, 1725, 1645, 1565 and 915 cm.$^{-1}$;
    (c) proton magnetic resonance spectrum in deuteriochloroform as shown in FIG. 2;
    (d) ultra-violet spectrum in methanol solution shows a characteristic absorption at 234 nm ($\epsilon=12900$) and 272 nm ($\epsilon=10800$);
    (e) melting point 176°–178° C.;
    (f) $[\alpha]_D^{23}=-82°$ (c=0.2 in methanol);

and the corresponding "free acid" form thereof of the molecular formula $C_{35}H_{54}O_8$, characterised by $R_F=0.55$ (approximately) on thin layer chromatography on silica gel (Merck's "Kieselgel 60F-254"—trade mark), 0.25 mm, thickness, developed with a mixture of diethyl ether, methanol and formic acid in the proportion 95:4:1 by volume; UV in ethanol 274 nm ($\epsilon=13900$), broad;

or other alkali metal salts which can be derived therefrom.

2. A process for the manufacture of the compounds claimed in claim 1, which comprises culturing an M.139603—producing strain of *Streptomyces longisporoflavus* identified as NCIB 11426 in an aqueous nutrient medium containing a source of assimilable carbon, under shaken aerobic conditions at a temperature of between 22° and 32° C., extracting the fermentation mixture thus obtained with a water-immiscible organic solvent by conventional means; and evaporating the solvent, to obtain the sodium salt, M.139603, may be converted to the "free acid", and the "free acid" may be converted to other alkali metal salts, by conventional means.

3. A process according to claim 2 which involves converting the sodium salt M.139603 to the free acid.

4. A process according to claim 3 which comprises converting the free acid to an alkali metal salt other than the sodium salt.

5. A method for increasing growth in domestic ruminant animals which comprises orally administering to the animals a compound as claimed in claim 1 in an amount effective to increase growth.

6. A composition for increasing growth in ruminant animals which comprises from 5 ppm. to 50% w/w of a compound as claimed in claim 1, together with a solid or liquid, edible non-toxic diluent or carrier.

* * * * *

UNITED STATES PATENT AND TRADEMARK OFFICE
CERTIFICATE OF CORRECTION

PATENT NO. : 4,279,894
DATED : July 21, 1981
INVENTOR(S) : DAVIES ET AL

It is certified that error appears in the above-identified patent and that said Letters Patent is hereby corrected as shown below:

Col. 10, lines 33-36, claim 2, delete ", may be converted to the free acid, and the free acid may be converted to other alkali metal salts, by conventional means".

Signed and Sealed this

Third Day of May, 1988

Attest:

DONALD J. QUIGG

*Attesting Officer*  *Commissioner of Patents and Trademarks*